United States Patent [19]

Heyman

[11] 4,363,242

[45] Dec. 14, 1982

[54] PULSED PHASE LOCKED LOOP STRAIN MONITOR

[75] Inventor: Joseph S. Heyman, Gloucester, Va.

[73] Assignee: The United States of America as represented by the Administrator of the National Aeronautics and Space Administration, Washington, D.C.

[21] Appl. No.: 199,767

[22] Filed: Oct. 23, 1980

[51] Int. Cl.$^3$ .................. F16B 13/02; G01H 1/00; G01N 29/00

[52] U.S. Cl. ........................... 73/761; 73/579; 73/597; 73/629

[58] Field of Search .............. 367/125; 343/7 PL; 73/579, 761, 801, 629, 597

[56] References Cited

U.S. PATENT DOCUMENTS

| | | | |
|---|---|---|---|
| 3,759,090 | 9/1973 | McFaul et al. | 73/801 |
| 3,812,709 | 5/1974 | Benson et al. | 73/597 |
| 4,014,208 | 3/1977 | Moore et al. | 73/761 |
| 4,062,227 | 12/1977 | Heyman | 73/801 |
| 4,117,731 | 10/1978 | Heyman | 73/589 |

OTHER PUBLICATIONS

Instrument for Continuous High Resolution Measurement by Blume in Review of Scientific Instruments, vol. 34, No. 12, Dec. 1963.

Conference: Proceedings of the Conference on Mechanical Properties of Materials at High Rates of Strain, by Jumpei Shioiri and Katsuhiko Sato, pp. 154–162, Oxford, England, Apr. 1974.

ISA Transactions, vol. 19, No. 2 in 1980; Measurement of Applied and Residual Stresses with Ultrasonic... by B. E. Gordon, Jr.

Primary Examiner—Edward H. Kazenske
Assistant Examiner—David V. Carlson
Attorney, Agent, or Firm—William H. King; John R. Manning

[57] ABSTRACT

The RF output of a voltage controlled oscillator (VCO) 11 is periodically gated by gate 15 to a transducer 18 which produces acoustic waves in bolt 19. The reflected acoustic waves are converted to electrical signals by transducer 18 and gated by a gate 20 to mixer 31. Mixer 31 also receives the output from VCO 11 and produces an output which is filtered by low pass filter 32. The output of filter 32 is a DC signal proportional to the phase difference change from a fixed phase difference between the two input signals to mixer 32. This DC signal is sampled at an instant and held by circuit 33 in response to the "P" signal. The output of circuit 33 is integrated by integrator 34 and then applied to VCO 11 to change the frequency of VCO 11 such that the phase difference between the two inputs to mixer 31 remains at said fixed phase difference. The frequency of VCO 11 is a measure of the change in strain of bolt 19.

10 Claims, 3 Drawing Figures

PULSED PHASE LOCKED LOOP STRAIN MONITOR

ORIGIN OF THE INVENTION

The invention described herein was made by an employee of the U.S. Government and may be manufactured and used by or for the Government for governmental purposes without the payment of any royalties thereon or therefor.

BACKGROUND OF THE INVENTION

The invention relates generally to a strain measuring device and more specifically concerns a device for measuring changes in strain of any materials (metals, composites, glass, rock, concrete, etc.) having many geometries (bolts, rods, plates, blocks, in situ mine shafts).

The prior art for determining fastener tension using torque depends on the repeatability and consistence of friction—a fact which is not achievable. Even for critical fasteners with extreme process control and care in storage and application, torque is capable of at best a nominal 15% variation in fastener strain with a given torque. In most applications, the errors obtained using torque are far greater due to the fact that up to 90% of the applied torque overcomes friction—only 10% goes into fastener strain. Thus a variation of 10% in friction can cause a 100% change in strain.

Other techniques, which are accurate, measure fastener elongation or direct strain. The simplist of these methods include micrometer measurements which are slow, require access to both sides of the fastener or a knowledge of the joint compliance and therefore are impractical. Electronic strain gaged bolts are costly and require highly stable bonds of the strain gage to the fastener for accuracy.

Ultrasonic techniques have been developed for bolt tension measurements which use shock excited acoustic pulse time of flight measurements or multiple pulse overlap/null methods or continuous wave high harmonic resonance techniques.

The shock excited methods are inherently broadband and thus launch an acoustic wave containing many frequencies. Each frequency propagates with a unique diffraction producing many different effective path lengths in the group velocity waveform. Also, this technique requires high speed electronics to achieve the accuracy necessary for bolt tension measurements (typically nanosecond resolution for a 10 cm bolt of round trip time $35 \times 10^{-6}$ sec or 3 parts in $10^4$).

The double pulse overlap method is difficult to automate and requires considerable judgment on the part of the user. Furthermore, this method is unnecessarily complicated and can easily be misread when cycle for cycle overlap is shifted by $2\pi$.

A gated RF tone burst technique has been disclosed which requires user judgment to achieve a proper phase locking point and an inability to maintain that locking point under sample changes without user input. In addition, this device does not take advantage of instantaneous phase measurement, but rather averages the phase signal over several microseconds. This produces greater instability for geometrically varying situations such as occur in a fastener under preloading. Furthermore, the time delay involved with using the integral of the sample during the phase gate does not allow use of layered samples with shifts occuring during the initial pulse propagation phase gate window.

A continuous wave (CW) method which depends on resonance techniques requires high Q fastener geometry to achieve an acoustic spectra free of structure which may cause locking errors. As the bolt geometry becomes nonideal, as may occur in a fastener with a hole, markings on its surface or rough nonparallel surfaces, the CW approach becomes impractical.

It is an object of this invention to provide a device for measuring changes in strain of any material having many different geometries.

Another object of this invention is to provide a device for measuring changes in strain in which no user judgment is necessary.

A further object of this invention is to provide a device for measuring strain that takes advantage of instantaneous phase measurements.

Still another object of this invention is to provide a device for measuring strain which is not easily misread when cycle for cycle overlap is shifted by $2\pi$.

A still further object of this invention is to provide a device for measuring the strain in a sample whose geometry is nonideal.

Other objects and advantages of this invention will become apparent hereinafter in the specification and drawings.

SUMMARY OF THE INVENTION

The invention is an instrument that uses a pulsed phase locked loop ($P^2L^2$) technique to measure changes in strain in a sample. The $P^2L^2$ technique propagates a gated Radio Frequency (RF) acoustic wave into the sample. The acoustic wave propagates through the sample, reflecting from an interface and returns to the point of origin. The instrument senses the pressure of the acoustic signal, gates the electrical signal from the sample that is produced by the reflected acoustic wave and samples the relative phase of the electrical signal by comparing its phase at an instant during each gating cycle with that of the continuously running voltage controlled oscillator (VCO) from which the initial driving signal was gated, A feedback loop is closed thus locking the frequency of the VCO to a fixed phase relationship with respect to the VCO. When the sample is loaded, strain plus sound velocity dependence on strain cause an acoustic phase shift producing a frequency shift in the VCO. The frequency shift $\Delta F$ divided by frequency F, ($\Delta F/F$) is linearly proportional to the applied load (for elastic loading). Thus, the device can be used to accurately measure changes in strain independent of fastener friction.

DETAILED DESCRIPTION OF THE INVENTION

Figure 1:
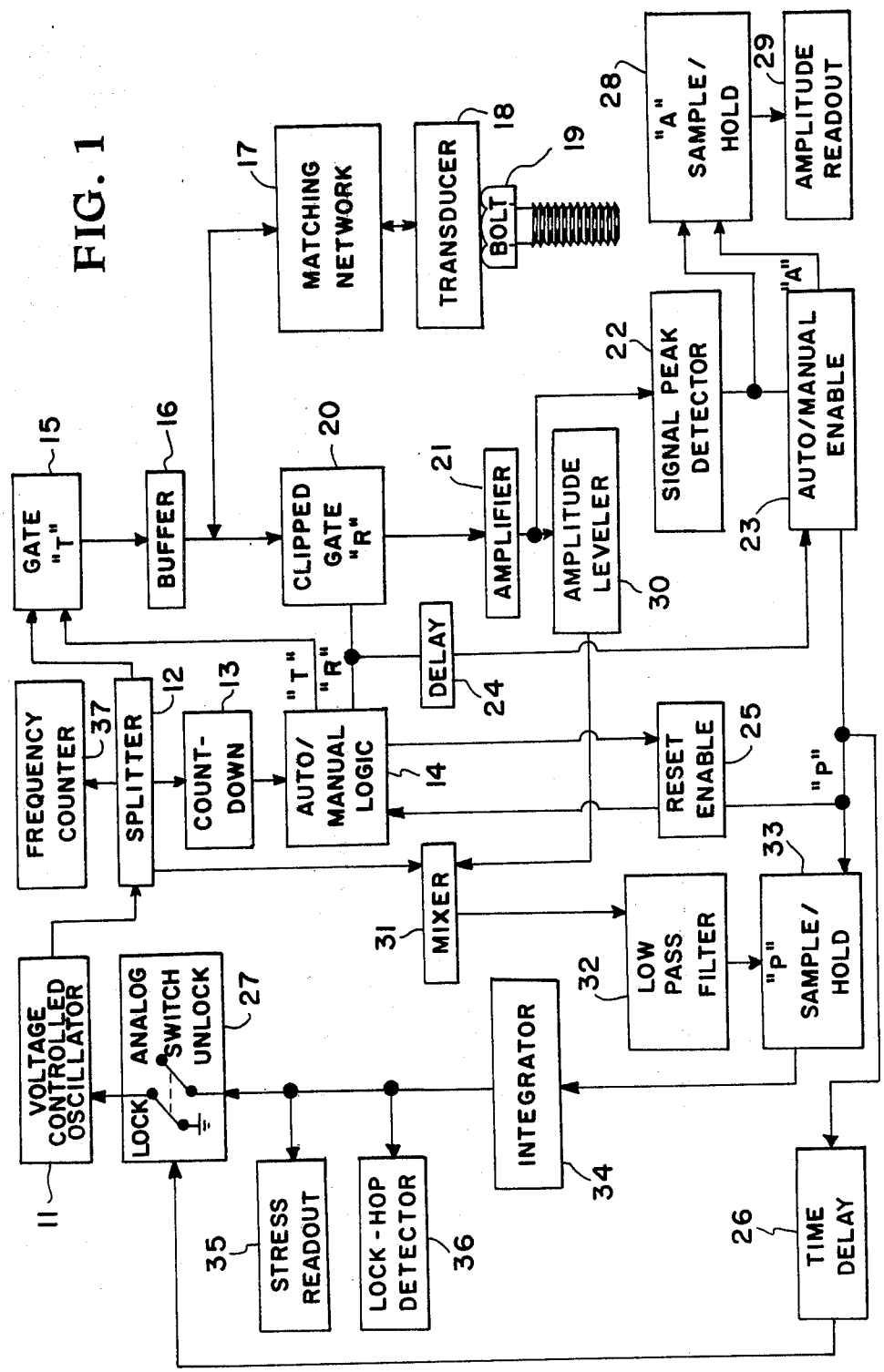
FIG. 1 is a block diagram of the invention.
Figure 2:
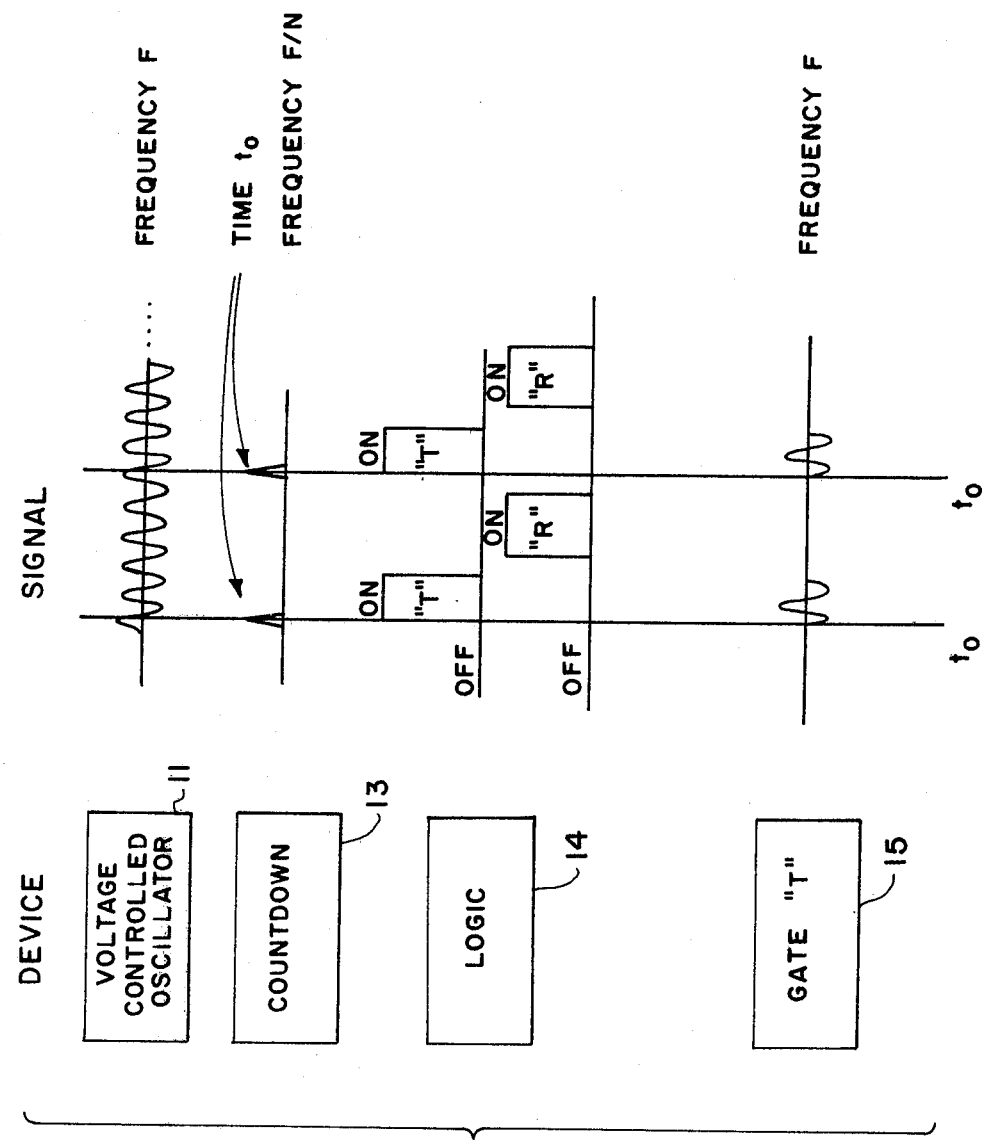
FIGS. 2 and 3 are diagrams of the outputs of some of the blocks shown in FIG. 1.

Turning now to the embodiment of the invention selected for illustration in the drawings the number 11 in FIG. 1 designates a voltage controlled oscillator (VCO) whose RF output is split into four isolated signals by a splitter 12. The VCO frequency is reduced by a count down circuit 13 which outputs a pulse after a certain number, N, of VCO cycles have passed with the pulse occurring at a fixed phase point of the VCO signal as shown in FIG. 2. The count down pulse starts a logic circuit 14 which outputs a sequence of signals that turns on and off transmitter gate "T" 15. The output of gate 15 is power amplified in a buffer 16 to drive a high signal level into the impedance of a matching network 17 which drives a transducer 18 producing an acoustic wave propagating in a bolt sample 19.

Figure 3:
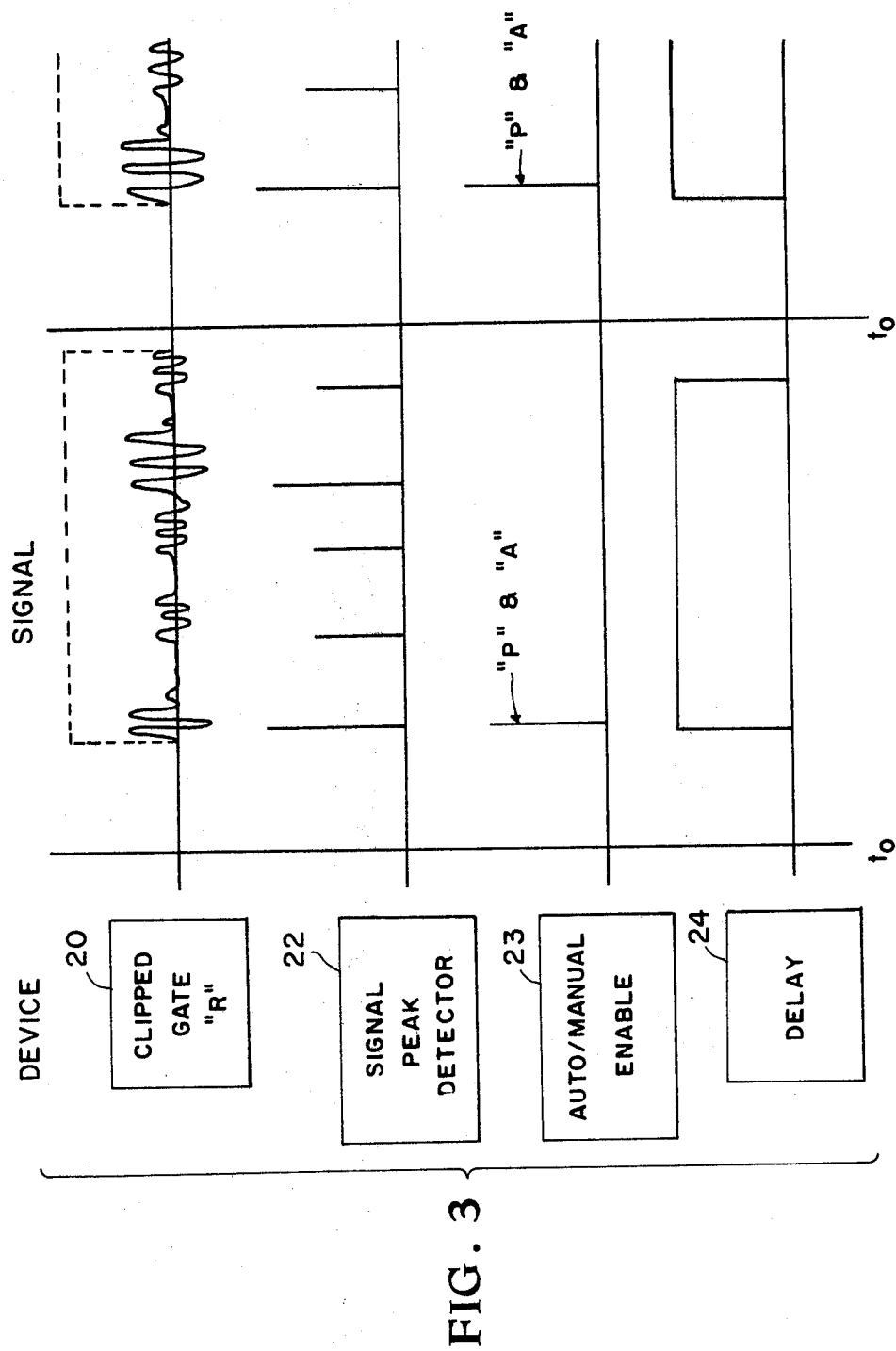

The acoustic signal in the bolt consists of several cycles of sound which reflect in the bolt (echo) and are converted to an electrical signal by transducer 18, electrically impedance matched in 17 and fed to a clipped gate "R" 20. The gate 20 prevents the high power buffer 16 from damaging an amplifier 21. Gate 20 is set to open by logic 14 when the desired echo from the bolt occurs. The output of gate 20 is amplified in amplifier 21 and peak detected by a peak detector 22, the output of which enters an enable device 23 which is told to fire once by a delay 24 all shown in FIG. 3. The output of enable device 23 fans out to four devices: reset enable 25 which arms logic 14 to allow it to continue to the next sequence of pulses; a time delay 26 which closes an analog switch 27 in a feedback loop to VCO 11 after an integrator 34 receives a signal; "A" sample hold 28 which measures the amplitude from peak detector 22 of the first echo and displays the amplitude in an amplitude read out 29; and "P" sample hold 33.

The signal to sample hold 33 is level processed in an amplitude leveler 30 to assure amplitude insensitivity when the signal enters a mixer 31. Mixer 31 which also receives an input from VCO 11, provides a sum and difference frequency output of the VCO frequency. Since the signals into the mixer are both at the VCO frequency a DC level and a 2F signal is obtained. The 2F is filtered in a low pass filter 32 and the remaining DC level which contains phase information (phase shift between the VCO and the returned echo) is sample held in 33 at the instant of the "P" pulse from enable 23.

The output from sample hold device 33 is integrated in integrator 34 and read out by a stress read out device 35. After pulse "P" from enable 23 has responded, the analog switch 27 locks and stays locked until 26 no longer continues to receive "P" pulses (several cycles of logic from logic 14). Should the locked loop momentarily lose signal and hop to a different phase stability point (a $2\pi$ phase shift), a lock-hop detector 36 signals faulty operation by sensing a sudden jump in the control voltage to VCO 11.

In automatic operation, if auto enable 23 does not receive a signal from peak detector 22 during the delay 24 window, a "P" pulse is not generated. Such a condition exists before the transducer is applied to the bolt. Reset enable 25, after a long delay (about 0.1 sec) with no "P" pulse, allows the cycle to start over with logic device 14 initiating a new sequence of signals. If, on the other hand, a pulse exists at peak detector 22, auto enable 23 sends out pulse "P" thus properly locking the pulsed phase locked loop ($P^2L^2$) automatically. Logic device 14 awaits the "P" pulse to activate reset enable 25 before it can start a new sequence on command from count down device 13.

Under both automatic and manual control, the output of the integrator 34 adjusts the frequency of the VCO 11 to a phase condition with respect to the signal which holds the integrator voltage constant—nominally zero volts out of sample hold 33. Should the phase shift in bolt 19 change, the frequency of VCO 11 shifts to maintain the locked condition. Thus the change in frequency of VCO 11 tracks changes due to fastener strain.

The change in frequency $\Delta F$ divided by frequency F of VCO 11 is directly related to the fastener change in strain:

$$\frac{\Delta F}{F} = \left( \frac{1}{V} \frac{dV}{dS} - \frac{1}{E} \right) \Delta S \tag{1}$$

where S is the fastener stress, V the velocity of sound, E the Young's modulus and dV/dS the change in sound velocity with stress. dV/dS has been shown to be equal to:

$$\frac{dV}{dS} = \frac{-1}{6\rho(\lambda + 2\mu/3)V} \left[ 2l + \lambda + \frac{\lambda + \mu}{\lambda}(4m + 4\lambda + 10\mu) \right] \tag{2}$$

where $\rho$ is the unstrained material density, $\lambda$ and $\mu$ are the Lamé constants and l and m are the Murnagham third order elastic constants. Rewriting equation (1):

$$\Delta S = \left[ \frac{\Delta F}{F} \right] K \tag{3}$$

where K is the stress acoustic constant and for a simple fastener under uniform axial strain is:

$$K = \left[ \frac{1}{V} \frac{dV}{dS} - \frac{1}{E} \right]^{-1} \tag{4}$$

K is a constant for a given material in its elastic range.

For the $P^2L^2$ technique, the locked loop maintains a constant phase condition. The total phase shift at frequency $F_1$ in a sample of acoustic transit time t, is:

$$\phi = 2\pi F_1 t_1$$

$$d\phi \equiv 0 = 2\pi(dF_1 t_1 + dt_1 F_1) \tag{5}$$

or simply:

$$\frac{\Delta F_1}{F_1} = \frac{-\Delta t_1}{t_1} \tag{6}$$

The $m^{th}$ harmonic resonance is defined as:

$$F_m = \frac{mv}{2a} = \frac{m}{t_1} \tag{7}$$

$$dF_m = \frac{-m dt_1}{t_1^2} = F_m \frac{dt_1}{t_1}$$

or $$\frac{\Delta F_m}{F_m} = \frac{-\Delta t_1}{t_1} \tag{8}$$

Thus, the $P^2L^2$ has a frequency that varies linearly with applied stress.

The functional blocks shown in FIG. 1 are all well within the skill of one having ordinary skill in the electronic art. Hence the details of these blocks are not disclosed in this specification.

The advantages of this invention over prior art strain measuring devices are: the strain in any material can be measured, the shape of the material sample can have many different geometries, no user judgment is necessary, no reading errors are made when cycle for cycle overlap is shifted by $2\pi$ and instantaneous phase measurements or comparisons are made.

The invention can be used with a two transducer system without any loss of generality. In addition, the stress read out can incorporate a microprocessor or other device to calculate actual $\Delta F/F$ values from the frequency counter and convert them into stress in MPa or PSI notation including proper calibration for K or bolt geometry.

What is claimed is:

1. An instrument for measuring changes in strain of a sample comprising:

transducer means attached to said sample for converting electrical signals into acoustic signals in said sample and for converting the acoustic signals reflected by said sample into electrical signals;

a continuous wave RF electrical source means for periodically gating said RF source to said transducer means;

means for periodically gating away from said transducer means the signals produced by the acoustic signals reflected by said sample such that the times that the signals are gated away from said transducer means do not overlap the times that the RF source is gated to said transducer means;

means receiving the RF signals from the RF source and said signals periodically gated away from said transducer means for producing a DC electrical signal proportional to the change from a fixed difference in phase of the two received signals;

means receiving said signals periodically gated away from said transducer means for producing a pulse during each period that signals are gated away from said transducer means and during a time that a reflected signal is received, the duration of said produced pulse being substantially less than the duration of the gating away time;

means receiving said DC electrical signal and said pulse for sampling said DC electrical signal at the time said pulse is received and holding the sampled signal until the next pulse is received; and means receiving said sampled and held signal for changing the frequency of said RF source to maintain said fixed difference between the phases of said RF source to maintain said fixed difference between the phases of said RF source and said signals periodically gated away from said transducer means whereby the changes in frequency of said RF source are proportional to the changes in strain in said sample.

2. An instrument according to claim 1 including means for measuring the frequency of said RF source to provide a measurement of the change in strain of said sample.

3. An instrument according to claim 1 wherein said RF electrical source is a voltage controlled oscillator.

4. An instrument according to claim 1 wherein said means for producing a DC electrical signal includes a mixer receiving said RF signal and said signals periodically gated away from said transducer means and a low pass filter connected to the output of said mixer.

5. An instrument according to claim 1 wherein said means for producing a pulse includes a signal peak detector receiving said signals periodically gated away from said transducer means and means for selecting one of the peaks produced by said signal peak detector during each of said gating away periods wherein said selected peak is said pulse.

6. An instrument according to claim 5 including means for measuring said selected peak for providing a change in strain of said sample.

7. An instrument according to claim 5 wherein said selected peak is the first peak during each said gating away period.

8. An instrument according to claim 1 wherein said means for changing the frequency of said RF source includes an integrator at the output of said sampling and holding means.

9. An instrument according to claim 8 including means for measuring the output of said integrator to provide a stress readout.

10. An instrument according to claim 8 including a lock-hop detector means at the output of said integrator for signaling faulty operation by sensng a sudden jump in the control voltage to the voltage controlled oscillator.

* * * * *